United States Patent [19]
Turner

[11] Patent Number: 4,798,215
[45] Date of Patent: Jan. 17, 1989

[54] HYPERTHERMIA APPARATUS

[75] Inventor: Paul F. Turner, North Salt Lake, Utah

[73] Assignee: BSD Medical Corporation, Salt Lake City, Utah

[21] Appl. No.: 935,936

[22] Filed: Nov. 28, 1986

Related U.S. Application Data

[63] Continuation-in-part of Ser. No. 590,030, Mar. 15, 1984, Pat. No. 4,638,813, which is a continuation-in-part of Ser. No. 405,947, Aug. 6, 1982, Pat. No. 4,672,980, which is a continuation-in-part of Ser. No. 136,506, Apr. 2, 1980, Pat. No. 4,462,412.

[51] Int. Cl.$^4$ .............................................. A61N 5/00
[52] U.S. Cl. ..................... 128/804; 128/736
[58] Field of Search ................... 128/399, 804, 736

[56] References Cited

U.S. PATENT DOCUMENTS

| | | | |
|---|---|---|---|
| 4,397,313 | 8/1983 | Vaguine | 128/399 |
| 4,572,190 | 2/1986 | Azam et al. | 128/804 |
| 4,632,128 | 12/1986 | Paglione et al. | 128/804 |
| 4,715,727 | 12/1987 | Carr | 128/804 X |

FOREIGN PATENT DOCUMENTS

| | | | |
|---|---|---|---|
| 2815156 | 10/1978 | Fed. Rep. of Germany | 128/804 |
| 2000335 | 1/1979 | United Kingdom | 128/736 |
| 2144634 | 3/1985 | United Kingdom | 128/399 |
| 8102841 | 10/1981 | World Int. Prop. O. | 128/804 |

Primary Examiner—Lee S. Cohen
Attorney, Agent, or Firm—Hubbard, Thurman, Turner & Tucker

[57] ABSTRACT

A hyperthermia apparatus includes a hyperthermia treatment subsystem, and a receiver subsystem combined to use jointly the parts common to both subsystems. The hyperthermia and receiver subsystems include, respectively, a power source and radiometer connected to a switch controlled by a central processing unit (CPU) to selectively connect either the power source and the radiometer to the common parts to complete the subsystems as follows. A power divider having output ports for feeding electromagnetic energy through a plurality of applicator circuits each circuit including a phase shifter connected to the power divider, a power regulating switch connected to the phase shifter, and an applicator connected to the power control switches. The power regulating switches are controlled also by the CPU. Thus, when the CPU connects the power source to the power divider the hyperthermia subsystem is complete for operation in the tissue heating mode; however, when the CPU connects the radiometer, the receiver subsystem is complete with the phase shifter and power divider operating as a phase focused power combiner. In a second embodiment a separate radiometer is connected to each antenna port. The received analog signals are digitized for time correlation using available algorithms in a high speed computer.

16 Claims, 5 Drawing Sheets

HYPERTHERMIA APPARATUS

RELATED APPLICATIONS

The present application is a continuation-in-part of United States application for Letters Patent, Ser. No. 590,030 filed Mar. 15, 1984 (now U.S. Pat. No. 4,638,813 issued Jan. 27, 1987) which is a continuation-in-part of United States application Ser. No. 405,947, filed Aug. 6, 1982 (now U.S. Pat. No. 4,672,980 issued June 16, 1987) which is a continuation-in-part of application Ser. No. 136,506 filed Apr. 2, 1980 (now U.S. Pat. No. 4,462,412 issued July 31, 1984).

BACKGROUND OF THE INVENTION

This invention relates to a hyperthermia apparatus and more particularly to an apparatus having combined hyperthermia treatment and noninvasive thermometry capabilities.

Known hyperthermia treatment systems include multiple applicators and multiple temperature sensors for controlling the operation of the hyperthermia system. The multiple applicators utilizing ultrasound or microwave energy in the direct contact operating mode are placed directly upon an elastic cooling belt containing a circulating cooling liquid to carry the heat of hyperthermia treatment away from the surface of the healthy tissue. The temperature sensors are implanted in the normal tissue in the vicinity of the tumor, as well as within the tumor. Systems involving the placement of temperature sensors within the body are referred to as invasive thermometry systems. Those persons skilled in the art desiring additional information for this system are referred to U.S. Pat. No. 4,397,314 issued Aug. 9, 1983.

A known instrument for detecting microwave energy and for giving an accurate measurement of the power density thereof is disclosed in U.S. Pat. No. 3,919,638 issued Nov. 11, 1975. This instrument is substantially unaffected by polarization or modulation of the electromagnetic waves and includes a planar array of parallel connected diode detectors each having a pair of antenna leads forming a dipole antenna. The diode array may include groups of diodes having different antenna lead lengths to detect different frequencies of microwave energy for a meter. The meter may be selectively switched between the outputs of the different groups.

Further, the potential use of multiple frequency band radiometry as a means of noninvasive sensing of one-dimensional temperature profiles is presented in an article entitled "Noninvasive Thermometry Using Multiple-Frequency-Band Radiometry: A Feasibility Study", Stavros D. Prionas and G. M. Hahn, Bioelectromagnetic 6:391-404, 1985 Alan R. Liss, Inc. The article discloses that microwave thermography has been extensively used for the detection of cancerous nodules. Operating frequencies in the range of 1.3 to 6.0 GHz (free space wavelengths in the range of 5 to 23 Cm.) have been employed. At these long wavelengths subcutaneous temperature measurement is possible and detection of superficial tumors in the brain and thyroid is, in principle, feasible.

The article further discloses that a computer tomographic approach using 10 GHz microwaves has been proposed as an alternative to mammographic examination. A self-balancing microwave radiometer for measuring the energy emitted from a heated volume within a single frequency band has been developed at the RCA laboratories. The power spectrum of thermal noise generated by a given temperature depth distribution is governed by Planck's law of blackbody radiation. The frequency spectrum of energy received at the surface of the human body is affected by the frequency dependent attenuation properties of the intervening tissues. Microwave radiometry (the technique of measuring noncoherent electromagnetic energy, in the microwave part of the spectrum, that is emitted or scattered by the medium under observation) can be used to measure the thermal noise emitted from a heated volume of biological tissue.

This article reports the analysis of the spectral content of this thermal noise and the comparison of the magnitude of the signal to the inherent threshold of noise detectability associated with an ideal microwave radiometer. In the analysis a one-dimensional temperature distribution model was assumed. In real situations, three-dimensional temperature distributions will be encountered. It is clear that to resolve such a three-dimensional temperature field with a reasonable amount of spatial resolution additional information will be needed. This additional information might be in the form of data acquired using different orientations of a signal receiving aperture or a properly phased array of receiving apertures. An intriguing alternative is to employ a phased array of receiving apertures that coherently detect the signal emanating from a point in space. In either case, well established signal processing algorithms could be used to convert the measured data to reconstruct the temperature distribution.

The use of "Radiometer Receivers for Microwave Thermography" was disclosed in an article of the same title by D. V. Land, University of Glasgow, Glasgow, Great Britain, published in the microwave journal, May 1983. A comparison or Dicke radiometer configuration is used. The receiver produces an output at the input switching or modulation frequency that is proportional to the difference between the source temperature detected by an antenna and the temperature of an internal reference load or noise generator.

Finally, the application of board-band correlation techniques to medical microwave thermography was studied and reported in an article entitled "The Thermal and Spatial Resolution of a Broad-Band Correlation Radiometer with Application to Medical Microwave Thermography", Joseph C. Hill et al., IEEE Transactions on Microwave Theory and Techniques, Vol. MTT-33, No. 8, August, 1985.

An essential difference between the present invention and the prior art is the use of elements common to a hyperthermia treatment system and a heat detecting system to produce a combined hyperthermia treatment and noninvasive thermometry apparatus.

An advantage of the combined hyperthermia treatment and noninvasive thermometry is the cost savings. Another advantage is the commonality of parts which enables utilization of the apparatus in the heating mode and the temperature measurement mode using the same apparatus parameter settings to produce quickly the desired results through selectively switching a power source and a radiometer into a circuit containing the common parts. Without combining of the devices it may be either impossible or impractical to non-invasively monitor deep temperatures during hyperthermia treatments.

SUMMARY OF THE INVENTION

Accordingly it is an object of the present invention to provide an apparatus capable of creating hyperthermia in body tissue and measuring temperature distributions within the treated volumes during the course of hyperthermia treatments. The tissue regions to be treated and monitored include even deep tissues in the central area of the human torso, limbs, and brain.

Another object of the invention is to provide a cost effective hyperthermia and thermometry apparatus.

Still another object of the invention is to provide a combined apparatus for heating selected tissue areas whose set up parameters can be used also for measuring the temperatures of the selected tissue areas.

Yet another object of the invention is to provide a hyperthermia apparatus which can be effectively used in either a treatment mode or a diagnostic mode or both.

Briefly stated the hyperthermia apparatus comprises a combined transmitter/receiver system for inducing hyperthermia in body tissue and for measuring noninvasively the temperature of the corresponding body tissue.

BRIEF DESCRIPTION OF THE DRAWINGS

The novel features which characterize the present invention are defined by the appended claims. The foregoing and other objects and advantages of the invention will hereinafter appear, and for purposes of illustration, but not of limitation, a preferred embodiment is shown in the accompanying drawings.

DESCRIPTION OF THE PREFERRED EMBODIMENTS

Figure 1:
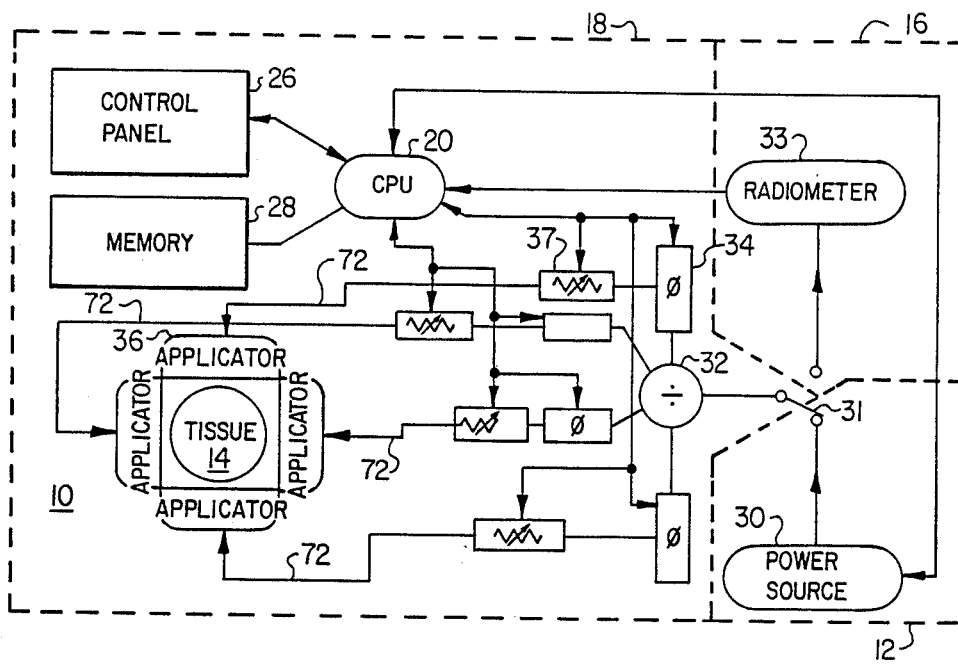
FIG. 1 is a schematic in block form of a first embodiment of the hyperthermia system constituting the subject matter of the invention.

FIG. 1 shows a block diagram of a hyperthermia treatment apparatus 10 having a subsystem 12 for creating hyperthermia in a target specimen 14 by means of electromagnetic radiation (EMR), a subsystem 16 for measuring noninvasively the temperature of the target specimen, and elements common thereto 18. The common elements include a central processor unit 20 which controls the system 10, and is in an interactive feedback relationship with each of its elements. The central processor unit (CPU) 20 accepts a plurality of inputs describing the present condition of the target 14.

A control panel or console 26 is coupled to the CPU 20 and is used by an operator to control a treatment and monitor its progress. The control panel 26 can be used to display any information obtained from the target 14 as well as all indicators of system operation. Various memory devices, represented by a single memory block 28, are coupled to the CPU 20. The memory 28 stores the result of pretreatment calculations which are used by the CPU 20 to control the progress of the treatment. Also, all pertinent operating data are stored in another part of the memory 28 as generated in order to have a complete record of the treatment process and results for future use.

For the hyperthermia subsystem 12, a high frequency energy source 30 is coupled to and controlled by the CPU 20. The source 30 is coupled through a switch 31 to a receiver such as a radiometer 33 for the receiver subsystem 16, and to power handling means including a power splitter 32, which constitutes a branch point in the power handling means in that it divides energy into a plurality of lines each having the same phase and power, a phase adjuster, and applicator connecting switches 37. The phase of the energy in each line shifter 34 manually or automatically. The output of each phase shifter 34 is coupled to one individual applicator 36 or a group of applicators. The actual delivery of power to the applicators 36 is controlled by switches 37 located between the phase shifters 34 and the applicators 36. The switches 37 may be simple on-off switches such as relays or solid state switches, or they may be digital or continuously variable attenuators or the switches 37 can also represent variable gain amplifiers. Like the source 30 and the phase shifters 34, the switches 37 are preferably controlled by the CPU during system operation, although the switches 37 may be manually operated. FIG. 1 shows only four phase shifters 34, applicators 36 and switches 37, but an actual system 10 may employ more of each to provide steering in several directions.

Figure 2:
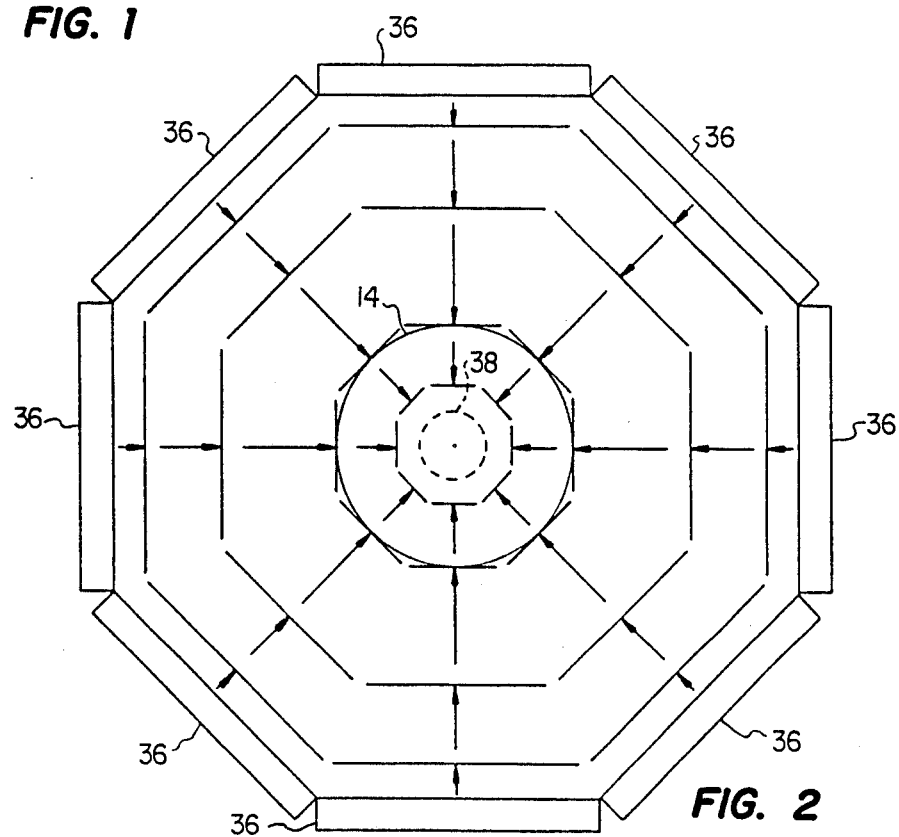
FIG. 2 is a diagram showing the method of operation of a system according to FIG. 1.

Referring to FIG. 2, eight individual applicators 36 are shown coupled together in an octagonal arrangement and surrounding a circular target 14. Each applicator 36 is diagrammatically represented by a rectangle. In reality, each applicator 36 would have a shape suitable for the emission of microwave EMR, several embodiments of which are shown in later drawings. FIG. 2 is a two-dimensional representation of a three-dimensional phenomena, with both the radiators 36 and target 14 extending for some distance perpendicular to the plane of the drawing. The radiation emitted from each applicator 36 is aligned so that the electric field component is perpendicular to the plane of the drawing and the magnetic field component forms circular equal potential lines which lie in the plane of the drawing. The stylized wave fronts shown in FIG. 2 by arrows approximate the direction of EMR emitted by the various applicators which is perpendicular to the electric and magnetic field component.

As the radiation emitted by the various applicators 36 converges on the target 14, it is seen that the electric fields of the radiation are lined up so that the target 14 sees, approximately, a converging circular wave front. The energy of the various wave fronts converges in the center of the target 14, where the electric field adds constructively and heats the center regions 38 of the target 14 to a greater degree than that caused by any one of the applicators 36 alone. This improved deep internal heating is caused without dangerously increasing the radiant energy density at the surface of the target 14, as the incoming energy is normally spread equally over the entire target surface. Thus, the energy imparted to the target 14 is concentrated near the center, when this is desired, and minimized to the extent possible at the target surface. Changes in amplitude and phase can displace the central energy focus to better heat a non-central target.

Figure 10:
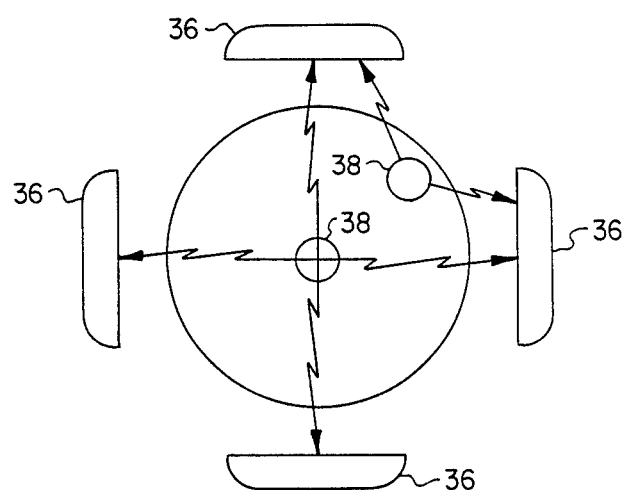
FIG. 10 is a partial view of the hyperthermia system showing the applicators with equal path to target with equal phase setting on phase shifters, and the non-equal path to non-target tissue.

As described in connection with FIG. 1, the energy radiated by each applicator 36 has a constant phase relationship with that emitted by the other applicators 36. This creates a synergistic result in the center area 38 of the target 14, whereby the center 38 is heated to a degree greater than that of a simple sum of the energy of the various applicators 36. The synergistic result will be described in more detail with relation to FIGS. 3 and 4. With all of the applicators 36 operating precisely in phase, the central heating area 38 will be symmetrical around the center point of a homogenous target 14. If the shape or location of the central heating region 38 is desired to be other than symmetrical about the center, changing the relative phase of the EMR emitted by the various applicators slightly will cause the central heating region 38 to move generally toward the applicators 36 which are phase-lagging the remainder (FIG. 10). By controlling the phase of energy emitted by the applicators 36 as described in connection with FIG. 1, it is therefore possible to manipulate the location of the central heating region 38 to best achieve the desired result. Manipulation of the central housing region 38 can also be accomplished through control of the power levels by controlling the switches, attenuators, or amplifiers 37. The power to each applicator 36 can be controlled as desired, through either on-off switches or continuously variable switches or attenuators as described above. Lowering or cutting off power to individual applicators 36 changes the shape of the central heating region 38, and the power absorbed at various points in the target 14 displace from the center 38 toward the higher power applicators.

Figure 3:
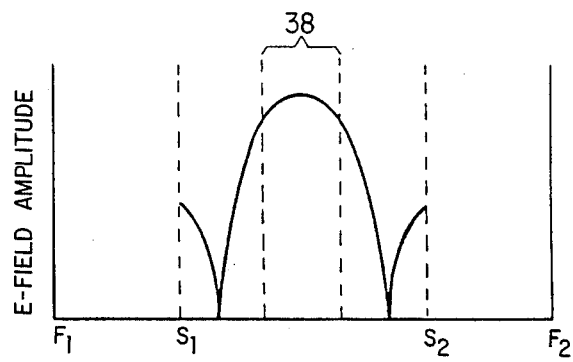
FIG. 3 is a diagram showing relative electric field amplitudes within a homogeneous target specimen.
Figure 4:
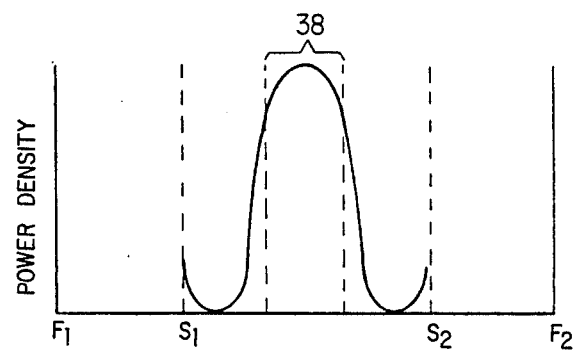
FIG. 4 is a diagram showing relative power density in a homogeneous target specimen.

FIGS. 3 and 4 show the mechanism by which the greatly increased power deposition in the central heating region 38 occurs. Considering any pair of diametrically opposed applicators 36 of FIG. 2, and a non-lossy homogenous target 14, the drawing of FIG. 3 shows the standing wave amplitudes of the E-field component of the EMR generated by such opposing pair on a line through the center of the target 14. The horizontal axis represents the distance between the opposing applicator emission faces, shown as points $F_1$ and $F_2$, and the vertical axis represents the amplitude of the alternating E-field standing wave at each distance. The points $S_1$ and $S_2$ represent the opposite surfaces of the target 14 with no consideration presently being made of the E-field external to the target 14.

Because the two oncoming wave fronts are of identical frequency and phase and have their E-fields aligned parallel to the center axis of the target 14, the electric field at each point between the applicators is the sum of the E-field vectors of each wave. When the frequency of the emitted radiation is chosen so that the wavelength in the target 14 is approximately three-fourths the diameter of the target 14, the amplitude of the standing wave caused by two applicators 36 in the target 14 is shown in FIG. 3. The maximum amplitude is located in the center region 38, with minimums being located one-fourth wavelength to either side of the center. The amplitude at the center is the sum of the amplitudes from each applicator 36, which for the two opposed apertures is twice the E-field created by a single applicator 36. When more than two applicators 36 are used, as shown in FIG. 2 for example, the resultant E-field sum is of course larger.

Testing has shown that best results are normally obtained when the wavelength of emitted EMR is between approximately ¾ and twice the target 14 diameter. This gives a relatively well-defined central heating region 38 and a good impedance match between the applicators 36 as described below and the target 14. Thus, for a target 14 diameter d, the preferred range of wavelengths can be found from the expression:

$$0.5\lambda_m \leq d \leq 1.3\lambda_m \tag{1}$$

where $\lambda_m$ is the wavelength in the tissue medium being heated. For high water content tissues, such as muscle and blood, the wavelengths at 100, 300 and 915 MHz are approximately 27, 11.9 and 4.5 cm. respectively. For low water content tissues the respective wavelengths at the frequencies are approximately 106.41 and 13.7 cm. If both types of tissue are present in a target, it is preferable to select a wavelength which satisfies equation (1) for the most prevalent tissue type (normally muscle tissue). A wavelength larger than suggested by equation 1 can be used if adequate impedance matching is obtained or provided by external matching techniques and nearly uniform surface vs. central heating can be expected.

FIG. 4 shows the relative power density at each point in the target 14 corresponding to FIG. 3. The power density is proportional to the square of the electric field strength, so that the power density curve shows a relatively sharp peak in the central heating region 38 for a non-attenuating medium. Heating at any point is due to the power absorbed at that point, which is in turn directly proportional to the power density at that point. Therefore, a heating cross section of the target has the same distribution as the power density curve of FIG. 4 when heat transfer effects are neglected. However, a medium capable of absorbing the radiant power is attenuating and will substantially reduce the central power density peak as represented in FIGS. 3 and 4 and increase the power density somewhat at the surface, resulting in near uniform heating being dependent on frequency, tissue diameter, and tissue conductivity. The centrally higher power density is still possible by proper frequency selection and antenna size.

Since the power density is proportional to the square of the E-field, a simple additive increase in the electric field at a given point results in an increase in the power density at that point by the square of the electric field. For example, in FIGS. 3 and 4 the electric field in the central heating region 38 resulting from 2 apertures is twice that due to a single applicator 36. Therefore, the power density of the central region is $2^2=4$ times the power density that would be caused by a single applicator 36. When, as in FIG. 2, more applicators 36 are used, the increase in power density becomes much greater than that caused by a single applicator 36. When eight applicators 36 are used, the E-field at the center is 8 times that caused by a single applicator 36 alone, and the power density at the center is therefore $8^2=64$ times the power density caused by a single applicator 36. This enormous increase in power density, and thus power absorbed, in the center of the target 14 is obtained without significantly increasing the power density at any one point on the surfce of the target 14. This phenomena, a synergistic result due to all applicators 36 operating at the identical frequency and with a predetermined phase relationship, allows deep heating of the target 14 without undesired excessive heating of the surface portions.

The above discussion of FIGS. 3 and 4 applies to non-lossy targets 14. In such targets 14 there is little energy absorption by the medium, so that the amplitude of the EMR from any given applicator 36 is undiminished as the radiation passes through. HOwever, actual targets 14 are lossy, so that the amplitude of EMR decreases as it passes through the target 14. In a typical case, the amplitude of the E-field at the center region 38 may be approximately 1/7 the E-field amplitude at the surface of the target 14. For the case of eight applicators 36, the power density in the center region 38 is approximately $8^2/7^2$ or approximately 1.3 times that at the surface of the target 12. It is important to note, however, that the power density in the center region 12 is still sixty-four times that which would be caused by a single applicator 36 alone. The general shape of the E-field and power density wave forms of FIGS. 3 and 4 still apply, with the actual peak value in the center region 38 being diminished with a lossy medium to nearly the same level as the surface in many cases. In general little is gained by using over 8 antennas if a non-lossy coupling medium is used to separate the antennas from the target.

The above-described synergistic increase in power density in the central heating region 38 occurs only when all applicators 36 radiate at the same frequency with the E-fields of the emitted EMR aligned. This E-field in phase alignment preferably occurs along the central axis of the target 14, which is perpendicular to the page as shown in FIG. 2. The E-field alignment of the various applicators 36 is preferably made as accurate as possible. However, some misalignment can be tolerated without unreasonably reducing the performance of the system 10. The vector sum of the E-field at any one point is equal to the sum of the individual E-field vectors. If a particular applicator 36 is misaligned, the EMR power emitted by that applicator contributes less to the synergistic power increase than an aligned field by a factor equal to the square of the cosine of half the angle between the misaligned E-field and the remaining E-fields. For small angles the cosine is close to one, so that small mismatches in the E-field alignment do not substantially degrade the synergistic power density enhancement which occurs in the central heating region 38.

When the various applicators 36 radiate energy at slightly different frequencies, it will become apparent to those skilled in the art that the various E-fields will not always add constructively, and the power density enhancement described above will not occur. In fact, in such a case, the power density in the central region 38 will be, at best, the simple sum of the individual applicator power densities. It is therefor important that the frequency of radiation emitted by all aplicators 36 be absolutely identical. For this reason, the preferred embodiment utilizes a single power source 30 and a power splitter 32 whereby the power supplied to each applicator 36 has the same frequency. While it is possible to use multiple sources providing that they can be precisely phase locked to emit identical frequencies, the practical considerations to accomplish this would complicate the system and add expense with little benefit, thus the preferred configuration requires only a single source 30 and splitter 32. It is not necessary that the frequency supplied to the applicators 36 be invariant with respect to time. In fact, it is desirable that the source 30 have a controllable frequency so that it may be adjusted to optimize performance with various target 14 materials as described above.

The shape and location of the central heating region 38 is determined by the distribution of applicators 36 in operation, the relative phase between them, the diameter of the tissue, the positioning of the tissue and the EMR frequency. It has been determined that the use of four or more uniformly spaced radiating applicators 36 will provide an approximately circular (ellipsoidal in three dimensions) central heating region 38. Eight radiating applicators 36 are used in FIG. 2 instead of four, because it has been determined that the power density, and thus heating, at the surface of the target 14 is more uniform than when only four radiating applicators 36 are used. An increase in the number of applicators 36 above eight does not appear to make a material difference in the operation of the system 10.

When all of the applicators 36 are precisely in phase, a symmetrical heating region 38 is formed in the precise center of a homogeneous target 12. Varying the relative phase of energy emitted by the various applicators 36 will cause the central heating region 38 to be shifted somewhat away from center toward the applicators 36 with lagging phase. The ability to alter the relative phase and amplitude between the applicators 36 is extremely useful, for example when a non-homogenous target 14 (such as an animal torso) is used. The wavelangth of the EMR will vary slightly in the different tissues of the target 14, and an alteration in emitted phase can compensate for the phase shifts thereby induced. Thus, when the target 12 has a known cross section of different tissues having known properties, the phase between the various applicators 36 can be adjusted to position the central heating region 38 at the desired location. Off-set positioning of the tissue can also compensate for non-homogenous effects on the heat pattern. The observations have shown, however, that the non-homogeneous tissues of the body have not significantly altered the central phase focus zone.

Figure 5:
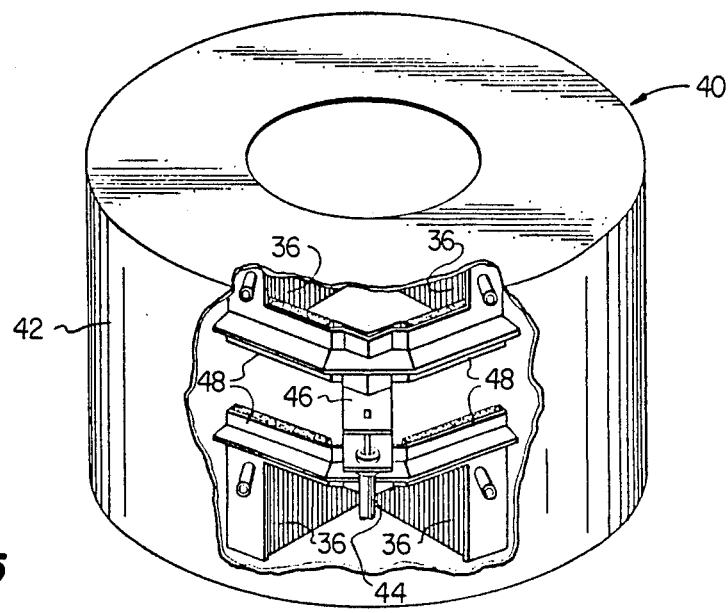
FIG. 5 is a partially cut away perspective view of one preferred applicator for use with the present invention.
Figure 6:
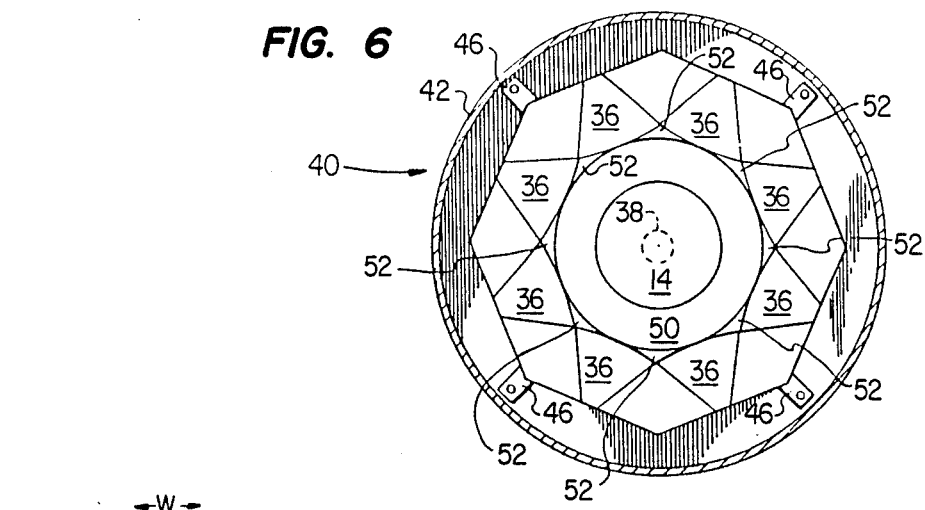
FIG. 6 is a top diagrammatic view showing operation of the applicator of FIG. 5.

One applicator array 40 suitable for use is shown in FIGS. 5 and 6. This annular array 40 comprises a battery of sixteen horn-type parallel plate waveguide antennae forming a folded dipole array being coupled together into two layers of eight radiators 36 each. For simplicity in construction, each input to the applicator array 40 feeds a two by two array of individual applicators 36. Thus, only four power inputs are needed for this sixteen applicator array 40.

It has been determined that the stacking of two or more applicators 36 in the E-field direction (perpendicular to the page in FIG. 2) still provides a substantially uniform electric field vertically but reduces the applicator size. It hs also been determined that stacking of the individual applicators 36 in an annular array 40 along the H-field (in the plane of the page in FIG. 2) provides a substantially uniform electric field around a target 14. Use of an array of individual applicators 36 allows each one to be sized and constructed so as to provide a good impedance match between the applicators 36 and the target 14. A detailed discussion of methods for fabricating horn-type applicators 36 suitable for use with the present invention is contained in pending U.S. Patent Application Ser. No. 136,506, filed on Apr. 2, 1980, now U.S. Pat. No. 4,462,42 and titled Annular Electromagnetic Radiation Applicator For Biological Tissue And Method, which disclosure is herein incorporated as if set forth verbatim.

The applicator array 40 is surrounded by a casing 42, which serves to support the individual applicators 36 in place and to decrease stray radiation, which can be hazardous. As shown in FIG. 5, the casing 42 is partially cut away, exposing portions of four separate applicators 36. A coaxial power input line 44 is coupled to a parallel plate waveguide 46. The waveguide 46 is coupled to four feed guides 48. The feed guides 48 are in turn coupled to four individual applicators 36, and have the same dimensions so that power is split evenly to the applicators 36. Each set of four applicators 36 therefore radiates energy having the same phase, power and E-field alignment.

FIG. 6 shows a top view of the applicator array 40. A target 14 is suspended interiorly of the array 40, and is surrounded by a bolus 50. The bolus 50 preferably contains deionized water, and is made from a flexible material so as to seal tightly around the target 14. Air gaps 52 may be left between portions of the bolus 50 and applicators 36, or the bolus may be manipulated to fill these gaps as desired.

The use of a bolus 50 has several important advantages. The fluid therein can be circulated through an external heat exchanger (not shown) to cool surface regions of the target 14. When deionized water is used in the bolus 50, there is very little power loss in the bolus 50, so that the full power raidated by the applicators 36 is delivered to the target 14.

Use of the bolus 50 improves the impedance match between the applicators 36 and the target 14. At the frequencies of interest, the impedance of a typical biological target 14 is approximately 44 ohms. The impedance of the applicators 36 and other electrical portions of the system is preferably 50 ohms in order to be compatible with standard components. The impedance of deionized water at the frquencies of interest is also approximately 44 ohms, so that all parts of the system 10 are inherently closely matched. If the water-filled bolus 50 were not present, a larger mismatch would occur at the radiating face of the applicators 36 and at the surface of the target 14. This mismatch occurs because the impedance of air is approximately that of free space, or 377 ohms. Any impedance mismatches cause reflections at the boundaries, lowering the percentage of radiated energy delivered to the target 14 and increasing stray radiation hazards.

As can be seen in FIG. 6, the applicator array 40 emits energy in the pattern discussed hereinbefore in connection with FIGS. 2 and 3, resulting in the power density pattern shown in FIG. 4. Thus, the applicator array 40 provides heating in the central region 38 without excessive heating of the surface regions.

Figure 7:
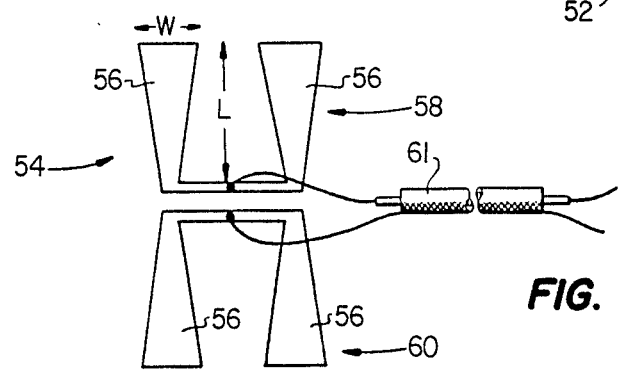
FIG. 7 is a diagram of a dipole antenna for use with the present invention.

An alternate embodiment of an applicator suitable for use with the present system 10 is shown in FIG. 7. This applicator 54 is essentially a dipole antenna pair sized for use with EMR of the frequencies contemplated. Each arm 56 of the upper and lower radiating portions 58, 60 acts as a single radiator in a manner similar to that of the annular array 40 of FIGS. 5 and 6. A coaxial feed line 61 is coupled to the center of the upper and lower radiating portions 58, 60, a balun can also be used to transform the coax-line to a balanced feed. When this applicator 54 is driven in a conventional manner, the E-field of the emitted radiation is aligned with the length of the arms 56.

Figure 8:
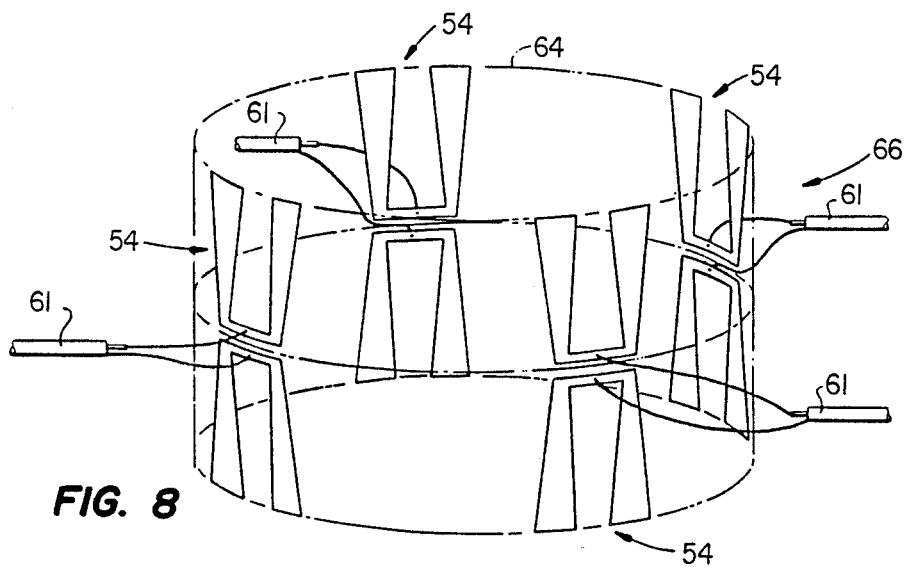
FIG. 8 is a perspective view of a folded dipole array for use with the system of the present invention.

The shape and size of the antenna arms 56 determine the optimum frequencies of operation and impedance characteristics of the dipole 54. It has been determined experimentally that a dipole 54 having tapered arms, wherein the ratio of arm width (W) to length (L) is maintained constant at approximately 0.087, gives a good impedance match with remainder of the system 10. When the dipole applicators 54 are combined into a cylindrical array 66 as shown in FIG. 8, and a water bolus (not shown) as similar to that discussed with FIG. 6 is used, a reasonably good 50 ohm impedance match is achieved. This approach tends to be more narrow band than the annular array of FIG. 5, but is much simpler to build.

Referring to FIG. 8, four dipole pair radiators 54 are assembled on a rigid, non-conducting frame 64 to form a cylindrical array 66. Each dipole radiator 54 is separately connected to the source 30 and power splitter 32 through a separte coaxial feed line 61. Each applicator 54 launches microwave EMR towards the center of the array 66 where the target specimen (not shown) is located. Preferably, a deionized water bolus (not shown) surrounds the target so as to better couple energy from the applicators 54 to the target, and to minimize reflections. The phase of the energy to each dipole applicator 54 can be controlled to vary the location of the central heating region 38 or to compensate for wavelength variations in non-homogenous targets as described in connection with FIG. 2.

Figure 9:
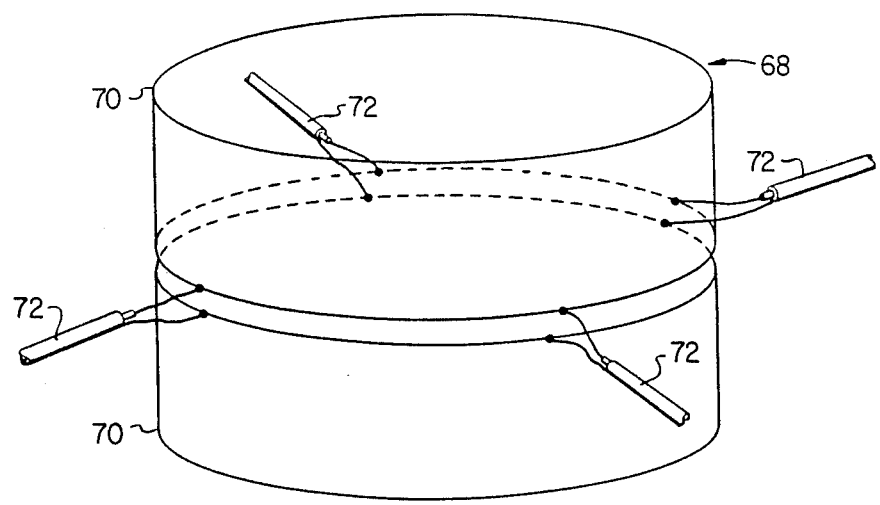
FIG. 9 is a perspective view of a third preferred applicator for use with the present invention.

Referring to the alternate embodiment of FIG. 9, a cylindrical dipole applicator 68 comprises two coaxial conducting cylinders 70 placed close together. These concentric cylinders 70 act as a single dipole applicator wherein the radiating arms comprise a flat radiating sheet which has been folded around to make contact with itself. The cylindrical dipole 68 will radiate toward its central axis, and constructive interference of the E-field will cause the synergistically increased power absorption in the central region 38 as described with the previous applicators. A single coaxial feedline 72 is sufficient to drive the cylindrical dipole 68. However, there will be some phase lag in the EMR emitted from the portions of the dipole 68 diametrically opposite the feedline 72. This will cause the central heating region 38 to shift somewhat away from the feedline 72 contacts. While this may be desirable in some cases, the preferred embodiment includes four coaxial feedlines 72 equally spaced around the dipole 68. When all four feedlines 72 are driven at the same phase, the central heating region 38 will be centered around the axis of the cylindrical dipole 68. Some manipulation of the central heating region 38 location can be made by varying the phase to the coaxial feedlines 72, but in general the degree of control will be less than that experienced with either the dipole array 66 or the horn radiator array 40.

Since the effective radiating aperture width of the cylindrical dipole 68 is equal to its circumference, and the height is limited by the size of the target to typically two feet or less, inherent impedance matching as was obtained with the dipole array 66 is difficult to achieve. Since the cylindrcal dipole radiator 68 will not be inherently matched with the impedance of the remainder of the system at most desirable frequencies, a conventional impedance matching device (not shown) should be used to minimize losses and reduce reflected power.

Both the folded dipole array 62 and the cylindrical dipole 68 emit radiation from both their inner and outer surfaces. An internal water bolus will increase the proportion of radiation emitted centrally, due to the better impedance match into the lower impedance fluid media. In order to reduce further the hazard of stray radiation, an outer conducting cylinder (not shown) can be placed around the cylindrical dipole 68 or dipole array 66. This outer shield can be grounded or left floating in order to reflect such radiation and reduce the outwardly emitted radiation. The reflecting shield must be spaced a sufficient distance from the cylindrical dipole 68 or dipole array 66 so that the ground plate will not capacitively load the aperture so much as to interfere with the primary emitted radiation distribution and reduce heating in the central region 38 or cause undesired non-central heating. In the preferred embodiment, the outer conducting cylinder is grounded and displaced so that minimal power pattern changes occur. Normally the space between the outer cylinder and the dipoles is filled with air or another low dielectric material thereby reducing the amount of energy coupled to the shorting cylinder. The grounding of the outer conducting cylinder is preferably done with a second coaxial outer shield dielectrically spaced from and outside of the coaxial outer conductor connecting to the dipole radiators.

In order to provide an effective hyperthermia treatment, the operator must be able to accurately determine the internal status of the target 14. For a living target 14, monitoring the vital signs gives a general indication of the health of the target 14 and indicates adverse events affecting its health. However, these signs, such as pulse, respiration, blood pressure and oral temperature, do not indicate whether enough heat is being applied to the region of interest to be effective.

Two additional measurements provide a fairly complete picture of the internal local effects of the hyperthermia treatment. The first of these is the measurement of actual temperature at selected points within the target 14. A real time thermal profile allows the operator to determine whether the desired regions of the target 14 are being heated to temperatures which are medically effective. Such a profile also allows the operator to ensure that no unwanted heating occurs in undesired portions of the target 12.

A serious limitation imposed on the use of hyperthermia treatment is the number, if any, of invasive temperature probes that can be inserted into deep-seated tumors to measure temperature distributions. Thus, if hyperthermia treatment applications are to expand, noninvasive thermography must provide the solution to the problems attending the use of invasive temperature probes. The hyperthermia subsystem described above provides the means through phased array apertures for producing high temperatures three dimensionally in the tumor without cold spots which are detrimental to the success of the treatment, while concommitently therewith producing lower non-destructive temperatures in the surrounding normal tissue. It has been found that warm living tissue emits blackbody radiation at depth indicating frequencies. Thus, the addition of a receiver subsystem 16 (FIG. 1) provides the means through a radiometer 33 to measure the blackbody radiation for producing a real time thermal profile.

Figure 11:
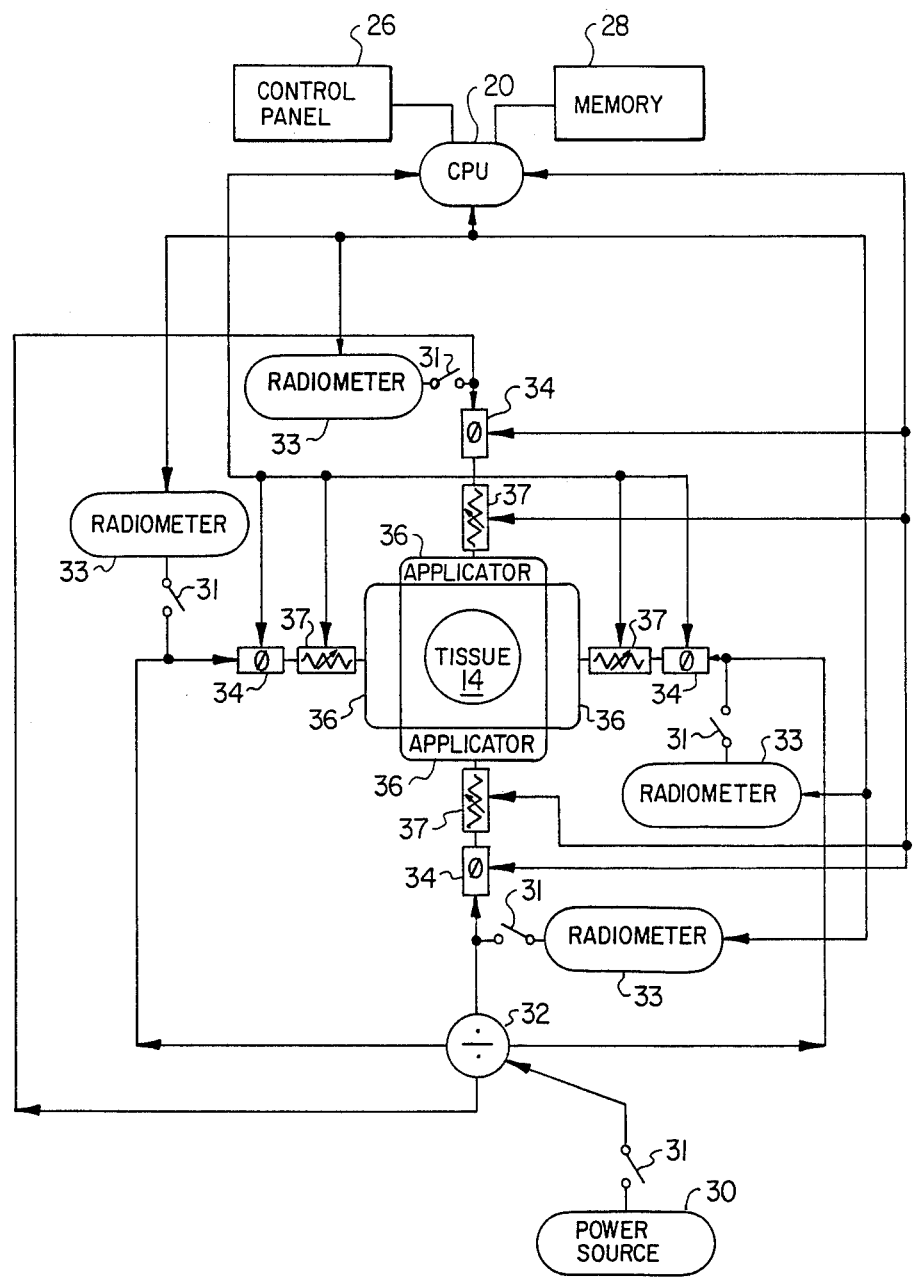
FIG. 11 is a schematic in block of a second embodiment of the invention.

In the receiver type subsystem 14, a single (cylindrical) dipole made from a double metal ring 68 (FIG. 9), for example, or four dipole antenna type applicators 36 (FIGS. 1, 10, and 11) are connected to the switch 31 (FIG. 1) for switching to the radiometer 33. A suitable radiometer is a Dicke-Switch radiometer which provides a very accurate and sensitive switching reference signal. The radiometer 33 is operable at single or multiple frequencies to obtain the temperature data.

Thus, in operation, all four coaxial cables 72 (FIG. 1) are switched either by the CPU 20 or manual manipulation of switch 31 from the power source 30 to the radiometer 33. The phase shifters 34 and power divider 32 then operate as a phase focused power combiner. This enables the radiometer 33 (FIG. 12) to coherently detect the blackbody noise source radiating from the area of focus. Just as in heating, for central focus the phase shifters 36 are equal and provide equal path lengths to target (FIG. 10). For off center focus, the phase shifters, if not adjusted, receive radiated energy from the non-target tissue with different phases and amplitudes. This would result in non-coherent summation of the signals in the combiner. To change the coherent phase target to the non-targeted tissue the phase shifters are adjusted to increase the delay from the coaxial cable connected closest to the target tissue. Thus, the amount of phase off-set (POS) is simply the difference in path length from the cylinder to the target zone from each coax location divided by the average tissue wavelength ($\lambda_m$) multiplied by 360 degrees.

$$POS = 360\,(d_1 - d_2/\lambda_m),\ \text{degrees}$$

In this way the coherent detection focus can be steered away from the center zone. Just as in the hyperthermia subsystem, a dielectric fluid bolus assures efficient transfer of the internally generated blackbody radiation.

By changing the receive frequency of the radiometer, the zone of the sensed thermal energy is changed. It will be appreciated by those persons skilled in the art that the diameter and shape of the tissue comprising the detection zone is altered by changing the radiometry received frequency.

Although each thermographic device must be calibrated with respect to the exact frequency, size, and detection zone, the basic relationship is that at the lower frequency ranges, such as, for example, 40 MHz to 70 MHz. The temperature measurement is related to the tissue volume encompassing substantially the whole human torso cross section. The relationship is the diameter of the tissue wavelength divided by 3.14. In muscle this is about 16 cm at 40 MHz and 13 cm at 70 MHz. However, owing to other tissues such as fat and bone, and air the average dielectric is two-thirds that of muscle. The result is an average wavelength ($\lambda_{ave}$) 1.2 times larger than that of muscle. Typical focal size areas of detection are set forth in Table 1.

TABLE 1

| MHz Frequency | $\lambda_m$ (cm) | $\lambda_{ave}$ (cm) | Focal size of Detection, CM | Penetration Depth, CM |
|---|---|---|---|---|
| 40 | 51.3 | 61.6 | 19 | 11.2 |
| 70 | 39 | 47 | 15 | 8.9 |
| 100 | 27 | 32.4 | 10 | 6.66 |
| 200 | 16.6 | 19.9 | 6.3 | 4.79 |
| 433 | 8.76 | 10.5 | 3.34 | 3.57 |
| 750 | 5.34 | 6.4 | 2.04 | 3.18 |
| 915 | 4.46 | 5.4 | 1.70 | 3.04 |
| 1500 | 2.81 | 3.4 | 1.07 | 2.42 |
| 2450 | 1.76 | 2.1 | 0.67 | 1.7 |

The applicator connection diagrams shown in FIGURE 1 demonstrate the use of the original annular array, multiple dipole array. As in the ring dipole, the deep tissue electromagnetic noise currents radiate energy which is received by the applicators 36 acting as antennae. The random blackbody energy radiates approximately the same signal in all directions. As the path length is about the same from the central tissue zone to each of the antenna receive ports, these fields will be approximately in-phase and are coherently summed as synchronous voltages. This coherent addition substantially enhances the voltage level at the radiometer.

As an example, the penetration depth in solid muscle is 6.66 cm at 100 MHz (Table 1). This means that plane waves would penetrate with an E-field strength decrease of 1/e at 6.66 cm compared with the skin surface. The absorption losses are then $-1.3$ dB/cm of depth. For a human torso 24 cm in diameter, even with solid muscle absorption, the field level at 12 centimeters of penetration would be $-15.65$ dB for a plane wave. This means that when the central emitted blackbody energy reaches the surface, it is $-15.65$ dB reduced by attenuation (causing a reduction in E-field of 17%). When this level is coherently summed by each antenna port, it results in a detected voltage of 66% compared to the same tissue volume and temperature at the surface. The apertures of the array provide coherent focusing of the detection zone. The close surface fields originating in separate zones are non-synchronous and therefore will not be enhanced by equal phase shifter settings. Thus, coherent reception enhances the ability to detect deeper temperatures and the non-coherent surface energy is not similarly enhanced by the summing detector.

The phase shift settings for off-set focusing (FIG. 10) are similar to those used to create off-set heating. The settings can be determined by geometric optic principles using tissue average wavelengths. For, example, at 100 MHz the average tissue wavelength is 32.4 cm. (obtained from Table 1). To shift the focal reception of heating zone off-center by 10 cm., the coaxial field nearest the focal shift is delayed the equivalent of 10 cm. and the opposite coax is led by the same amount. The degree of phase shift is determined by multiplying the distance of the off-set by 360 degrees and dividing by the average tissue wavelength. The port or cable connected to the antenna nearest the off-set would be delayed 115 degrees at 100 MHz and the opposite port would be adjusted to lead by 115 degrees. In this way signals being created in either the heating mode or received in the measuring mode would have a 10 cm. off-set.

In both modes the amplitude of the leading phase channel could be attenuated for more selective focal zone shifting. The attenuation amount can be stored in tables or memory for manual or automatic setting. Measured data on each antenna used is used to correct the table as antenna mutual coupling could effect the amplitude distribution and phase settings. If the switch devices 37 are variable gain amplifiers, it is necessary to by-pass these devices with a switch in a receive mode. This switch must be a very high isolation switch if the amplifiers are high gain to avoid undesireable amplifier feedback.

The central processor 20 causes the thermal information taken during operation of the system 10 to be stored in long-term memory (e.g., disk) for later analysis. The system 10 also uses this information in a feedback loop to control the operation of the power source 30 and splitter 32. If heating should rise to dangerous levels, the power applied to the target 14 can be decreased. Likewise, if the heating is insufficient, extra power can be applied. The CPU 20 can also display a temperature vs position plot for the operators to view.

In another embodiment (FIG. 11) separate frequency variable radiometric receivers 33 are connected to each antenna port. In this embodiment the signals are digitized and time correlated using available algorithms and a high speed computer. A high isolation switching device is required to protect the radiometers during active heat. Because more accurate tissue location and temperature is possible, these radiometric and antenna devices can be used in a diagnostic mode with no external heating.

This hyperthermia apparatus can be used also in the heating mode to noninvasively measure blood flow in the deep tissues of the body with the radiometer making thermal images thereof. This is possible by making thermal images before and after applying power for a short time (30 to 60 seconds). The difference between the images would represent the change in tissue temperature. If the lower frequencies have uniformly heated the cross-section, the resulting difference image would represent blood flow cooling between tissues of high water content. Reduced blood flow is a sign of large necrotic tumors. This test is usable to optimize frequency, phase and amplitudes during a hyperthermia treatment.

It is important that a very low noise radiometer be used and that adequate integration times be allowed in order to measure the small tissue signals. As the prior art references indicate, such radiometric receivers are available, but the known techniques do not include the combination of these sensitive devices with deep heating phased array therapeutic heating devices to provide a very useful hyperthermia apparatus. Nevertheless, known background noise cancelation circuits presently exist which can be included to improve the signal to noise ratio.

Although several embodiments of the invention have been described, it will be apparent to a person skilled in the art that various modifications to the details of construction shown and described may be made without departing from the scope of this invention.

What is claimed is:

1. A hyperthermia treatment apparatus comprising:
   a combined transmitter/receiver means for selective operation in a coherent heat mode and a coherent heat measuring mode, said combined transmitter/receiver means including a transmitter means for inducing electromagnetic energy in an electric field summing manner to a selected subcutaneous area of body tissue for heating, and a noninvasive receiver means for coherently combining blackbody radiation energy emitted from the selected subcutaneous area of the body tissue at depth indicating frequencies for measurement wherein the temperature of the selected subcutaneous area of body tissue being heated is monitored.

2. A hyperthermia treatment apparatus according to claim 1 wherein the combined transmitter/receiver means includes an antenna means for surrounding a preselected area of body tissue for inducing electromagnetic wave energy in phase into the subcutaneous area of body tissue for heating, and for receiving black body radiation energy emitted by the subcutaneous area of body tissue being heated, a plurality of power channels operatively connected to the antenna means for selectively feeding electromagnetic wave energy to the antenna means, and for summing the energy received therefrom, a switching means operatively connected to the plurality of power channels, a source of electromagnetic energy and a radiometer connected to the switching means, said switching means for selectively connecting the source of electromagnetic energy and radiometer to the plurality of power channels for transmitting electromagnetic wave energy through the plurality of power channels to the antenna means and for receiving energy therefrom, respectively, for coherent operation in the heating and heated tissue temperature measuring modes.

3. A hyperthermia treatment apparatus according to claim 2 wherein the plurality of power channels each include a phase shifter connected to the antenna means and a power divider connected to the phase shifter, said phase shifter and power divider for forming a phase focused power combiner when operating in the heated temperature measuring mode.

4. A hyperthermia treatment apparatus according to claim 3 wherein the antenna means includes a plurality of applicators and each of the plurality of power channels further includes a power control means having a switching means selected from the group consisting of on-off switches, relays, variable power attenuators, and variable gain amplifiers operatively connected to and between the phase shifter and an applicator of the plurality of applicators for controlling the delivery of power to the applicators wherein the location of the target within the subcutaneous area of the body tissue is determined.

5. A hyperthermia treatment apparatus according to claim 4 wherein the combined transmitter/receiver means further includes a central processing means operatively connected to the switching means of the power control means and/or phase shifter for setting the operating point of the power control means.

6. A hyperthermia treatment apparatus according to claim 5 wherein the central processing means is further connected to the source of electromagnetic energy and radiometer for selectively connecting the source of electromagnetic energy and the radiometer to the power divider.

7. A hyperthermia treatment apparatus according to claim 2 wherein the antenna means includes first and second cylindrical dipole rings connected through the plurality of power channels to the source of electromagnetic energy and to the radiometer selectively for injecting electromagnetic wave energy into the subcutaneous area of body tissue where it sums for heating and for receiving energy emanating at a depth indicating frequency from the heated subcutaneous area for measurement by the radiometer.

8. A hyperthermia treatment apparatus according to claim 2 wherein the antenna means includes a plurality of opposing applicators connected to the plurality of power channels.

9. A hyperthermia treatment apparatus according to claim 8 wherein the plurality of power channels each include a power control means for selectively controlling the amount of electromagnetic energy applied to each applicator for selectively locating a targeted area within the subcutaneous area of body tissue.

10. A hyperthermia treatment apparatus according to claim 2 wherein the radiometer is a single channel radiometer for generating temperature data at a preselected frequency.

11. A hyperthermia treatment apparatus comprising: a power means for generating electromagnetic wave energy, measuring means for measuring coherent radiant energy, switching means connected to the power means and measuring means for switching there between, power handling means connected to the switching means, and a plurality of applicators connected to the power handling means, said power handling means for producing a preselected distribution of the electromagnetic wave energy in a preselected phase relationship for the plurality of applicators when connected to the power means and for coherently combining radiant energy received from the plurality of applicators when connected to the measuring means, and said plurality of applicators selectively connected to the power handling means for focusing the distributed electromagnetic wave energy in a tissue target area, and receiving radiant energy emanating from the tissue target area, wherein the focused energy is summed coherently for forming a hot spot in the tissue target area in a heating mode, and the radiant energy emanating from the tissue target area is combined into coherent radiant energy for measurement by the measuring means in a heat measuring mode.

12. A hyperthermia treatment apparatus according to claim 11 further including a central processor means having means connected to the switching means for connecting selectively the power means and measuring means to the power handling means.

13. A hyperthermia treatment apparatus according to claim 11 wherein the measuring means for measuring coherent radiant energy includes a radiometer.

14. A hyperthermia treatment apparatus according to claim 11 wherein the power handling means includes a power splitter/combiner for selectively dividing and combining electromagnetic wave energy, a plurality of phase shifters connected to the power splitter/divider for phase selection, and a plurality of switching means connected to the plurality of phase shifters for controlling the delivery of electromagnetic wave energy selectively to and from the plurality of applicators.

15. A hyperthermia treatment apparatus according to claim 14 further including a central processor means having means for selectively controlling the plurality of switching means of the power handling means.

16. A hyperthermia treatment apparatus according to claim 15 wherein the central processor means includes means for controlling the phases of the plurality of phase shifters.

* * * * *